United States Patent [19]

Wolf et al.

[11] Patent Number: 5,554,742

[45] Date of Patent: Sep. 10, 1996

[54] PREPARATION OF ALKYL GLYCOSIDES

[75] Inventors: Gerhard Wolf, Mannheim; Alfred Oftring, Bad Durkheim; Georg Schuh, Ludwigshafen; Helmut Wolf, Hassloch; Rudolf Alt, Ludwigshafen; Hans-Heinrich Bechtolsheimer, Dittelsheim-Hessloch; Dieter Hertel, Leimen, all of Germany

[73] Assignee: BASF Aktiengesellschaft, Ludwigshafen, Germany

[21] Appl. No.: 295,795

[22] PCT Filed: Apr. 1, 1993

[86] PCT No.: PCT/EP93/00791

§ 371 Date: Sep. 15, 1994

§ 102(e) Date: Sep. 15, 1994

[87] PCT Pub. No.: WO93/21196

PCT Pub. Date: Oct. 28, 1993

[30] Foreign Application Priority Data

Apr. 10, 1992 [DE] Germany .......................... 42 12 080.2

[51] Int. Cl.$^6$ .............................. C07H 1/00; C07H 15/04
[52] U.S. Cl. ................................. 536/18.6; 536/18.5
[58] Field of Search .................... 536/18.6, 18.5

[56] References Cited

U.S. PATENT DOCUMENTS 4,721,780  1/1988  McDaniel, Jr. et al. .
4,996,306  2/1991  McDaniel, Jr. et al. .

FOREIGN PATENT DOCUMENTS 0096917  12/1983  European Pat. Off. .
0362671   4/1990  European Pat. Off. .
0252241   3/1992  European Pat. Off. .
3927919   2/1991  Germany .

Primary Examiner—Gary L. Kunz
Attorney, Agent, or Firm—Oblon, Spivak, McClelland, Maier, & Neustadt, P.C.

[57] ABSTRACT

The preparation of alkyl glycosides by reaction of aqueous glycoses having a water content of 10–80% by weight with aliphatic primary alcohols having from 5 to 30 C atoms is described, in which (a) the alcohols and the glycoses are employed in a molar ratio of 2:1 to 10:1, (b) 0.1–5% by weight, based on the amount of the glycoses employed, of the acidic form of an anionic surfactant is used as the acidic catalyst having emulsifying properties, (c) 1–30% by weight, based on the amount of the glycoses employed, of alkyl glycosides is used as a further emulsifier, (d) the aqueous glycose is preheated to 50°–90° C. and the preheated aqueous solution of the glycose is metered with effective mixing into the reaction mixture of alcohol, acidic catalyst and emulsifier in such a manner that an emulsion is formed, (e) the reaction is carried out at from 100° to 150° C. and from 10 to 100 mbar, the water introduced into the reaction mixture and the water formed by the reaction being continuously removed by distillation, (f) after the reaction has ended, the acidic catalyst is neutralized by addition of a base such that the resulting mixture has a pH of 8–10, then (g) the excess alcohol is removed by distillation at from 0.01 to 10 mbar down to a residual content of less than 5% by weight, based on the amount of alkyl glycoside present, and (h) the reaction mixture is bleached at pH 8–10 after conversion into an aqueous paste having a content of from 30 to 70% by weight of alkyl glycoside using a compound eliminating active oxygen.

3 Claims, No Drawings

PREPARATION OF ALKYL GLYCOSIDES

PREPARATION OF ALKYL GLYCOSIDES

The present invention relates to an improved process for preparing alkyl glycosides by reaction of aqueous glycoses having a water content of 10–80% by weight with aliphatic primary alcohols having from 8 to 30 C atoms.

Surface-active alkyl glycosides, which are mainly used in the detergent and cleaner sector, have been known for a long time and are prepared on the industrial scale by two different types of process. Either the long-chain alcohol component is directly linked to the sugar component with elimination of water by direct synthesis or a short-chain alkyl glycoside is first prepared as intermediate by the transacetalization method and is then reacted in a second step by transacetalization with long-chain alcohols to give the surface-active alkyl glycoside. However, the transacetalization method has a number of disadvantages in principle compared with direct synthesis, such as the additional use of a short-chain alcohol, a poorer space-time yield or the formation of relatively complex product mixtures.

EP-A 0,252,241 may be mentioned as an example of the transacetalization method. According to this, butyl oligoglycosides are prepared by acid-catalyzed reaction, for example using sulfuric acid or p-toluenesulfonic acid, of aqueous saccharide syrups with the addition of butyl oligosaccharides. The short-chain butyl glycosides can then be subjected to a transacetalization to give longer-chain alkyl glycosides.

In EP-A 0,362,671, and also in the references cited below, a direct synthesis of longer-chain alkyl glycosides is described. This specification recommends the use of acidic catalysts such as sulfuric acid, phosphoric acid or aliphatic or aromatic sulfonic acids for the acetalization reaction. The glycoses used for the reaction, such as glucose, should be as anhydrous as possible. The reaction is carried out, for example, by adding a suspension of the glycose in a fatty alcohol continuously to a mixture of acidic catalyst and fatty alcohol and at the same time removing the resulting water of reaction by distillation under reduced pressure.

A process is described in EP-A 0,096,917 in which a monosaccharide, such as glucose, suspended in a fatty alcohol is added continuously or in portions to a mixture of fatty alcohol and an acidic catalyst such as sulfuric acid or toluenesulfonic acid at from 80° to 150° C. in such a manner that no more than 10% of unreacted monosaccharide is present in the reaction mixture. Anhydrous glucose of a specific particle size is employed.

As the acidic catalyst for the direct synthesis of alkyl glycosides, EP-B 0,132,043 recommends the acid form of an anionic surfactant, by whose use instead of customary catalysts, such as sulfuric acid or p-toluenesulfonic acid, it is intended to improve the color quality of the product and to reduce the content of undesired polysaccharides in the final product. In the process of this reference only a small excess of fatty alcohol is employed, preferably 2 mol of fatty alcohol per mole of glucose, which is used in its anhydrous form, and during the neutralization of the acidic catalyst with a base a pH of from 6.6 to 7 is maintained.

WO-A-90/07516 and DE-A 3,927,919 also describe the use of surface-active acidic catalysts of this type, dinonylnaphthalenesulfonic acid or sulfosuccinic acid, to obtain an alkyl glycoside having a paler color and a low content of polysaccharides.

US-A-4,721,780 describes a process for preparing alkyl polyglucosides in which aqueous monosaccharide solutions are reacted with monohydric $C_2$- to $C_6$-aliphatic alcohols in a homogeneous aqueous phase in the presence of acidic catalysts at from 60° to 200° C. and water is removed from the reaction mixture in such a manner that a separate phase of an aqueous monosaccharide solution is not formed.

A corresponding process is disclosed in U.S. Pat. No. 4,996,306 for the preparation of $C_7$- to $C_{30}$-alkyl polyglucosides, in which aqueous mono- or oligosaccharide solutions are reacted with $C_7$- to $C_{30}$-alcohols in a homogeneous, single-phase aqueous reaction medium. In this process too, the formation of a separate phase which consists of an aqueous saccharide solution should be avoided. The examples of U.S. Pat. No. 4,996,306 however relate only to the acid-catalyzed reaction of aqueous saccharide solutions with n-propanol, n-butanol or mixtures of n-butanol and methanol, methanol being employed to improve the miscibility of the reactants in order carry out the reaction in the homogeneous phase.

The alkyl glycosides-prepared by the processes known from the prior art, however, still have a number of disadvantages. As a rule, they are still too highly colored and often have a hydrophilic/hydrophobic ratio which is too unfavorable. It is in particular desired in the case of alkyl glycosides to shift the hydrophilic/hydrophobic ratio in favor of the hydrophobic moiety. This is best achieved by a controlled synthesis of alkyl monoglycosides and avoidance of the alkyl oligo- and polyglycosides. The higher the content of the alkyl monoglycosides, naturally the more hydrophobic the behavior of the product.

Additionally, a further simplification of the preparation process for alkyl glycosides is desired. The preparation process, even on the industrial scale, should be highly efficient, problem-free to carry out and economical. In particular, it should be possible to use easily accessible feedstocks.

It is an object of the present invention to provide an improved preparation process for alkyl glycosides which yields products having improved properties and is efficient, problem-free to carry out and economical.

We have found that this object is achieved using a process for preparing alkyl glycosides by reaction of aqueous glycoses having a water content of 10–80% by weight with aliphatic primary alcohols having from 8 to 30 C atoms, if (a) the alcohols and the glycoses are employed in a molar ratio of 2:1–10:1, (b) 0.1–5% by weight, based on the amount of the glycoses employed, of the acidic form of an anionic surfactant is used as the acidic catalyst having emulsifying properties, (c) 1–30% by weight, based on the amount of the glycoses employed, of alkyl glycosides is used as a further emulsifier, (d) the aqueous glycose is preheated to 50–90° C. and the preheated aqueous solution of the glycose is metered with effective mixing into the reaction mixture of alcohol, acidic catalyst and emulsifier in such a manner that an emulsion is formed, (e) the reaction is carried out in emulsion at from 100° to 150° C. and from 10 to 100 mbar, the water introduced into the reaction mixture and the water formed by the reaction being continuously removed by distillation, (f) after the reaction has ended, the acidic catalyst is neutralized by addition of a base such that the resulting mixture has a pH of 8–10, then (g) the excess alcohol is removed by distillation at from 0.01 to 10 mbar down to a residual content of less than 5% by weight, based on the amount of alkyl glycoside present, and (h) the reaction mixture is bleached at pH 8–10 after conversion into an aqueous paste having a content of 30–70% by weight of alkyl glycoside using a compound eliminating active oxygen.

In the following, alkyl glycosides are understood as meaning the reaction products of sugars and aliphatic alcohols, suitable sugar components in the following being aldoses and ketoses designated as glycoses, for example glucose, fructose, mannose, galactose, talose, gulose, allose, altrose, idose, arabinose, xylose, lyxose or ribose. Because of the better reactivity, the aldoses are preferably used. Among the aldoses, glucose is particularly suitable because of its easy accessibility and availability in industrial quantities. The alkyl glycosides which are preferably prepared by the process of the invention are therefore the alkyl glucosides.

The term alkyl in alkyl glycoside includes the radical of a primary aliphatic alcohol of chain length $C_8$ to $C_{30}$, in particular of a fatty alcohol obtainable from natural fats. The terms alkyl oligoglycoside, alkyl polyglycoside, alkyl oligosaccharide or alkyl polysaccharide relate to those alkylated glycoses in which an alkyl radical is bonded to more than one glycose radical, i.e. to a poly- or oligosaccharide radical, in the form of the acetal. These terms are regarded as synonymous with one another. Accordingly, an alkyl monoglycoside is the acetal of a monosaccharide. Since mixtures are in general obtained in the acid-catalyzed reaction of sugars and aliphatic alcohols, in the following both alkyl monoglycosides and alkyl poly(oligo)glycosides and in particular mixtures thereof, including possible secondary components such as, for example, fructosides, are understood under the term alkyl glycoside.

In the process of the invention it has been found that in the synthesis of long-chain alkyl glycosides by the direct procedure anhydrous glucose, which on the one hand can only be prepared in a complicated manner and on the other hand is difficult to handle, or starch, which has to be subjected to a degradation reaction beforehand and therefore requires cosolvents, no longer has to be employed, but aqueous glucose (dextrose syrup) can be used. An aqueous glucose solution of this type is obtained in the enzymatic or acidic hydrolysis of starch, for example potato, corn or wheat starch, and may contain a variable content of free glucose. Thus, the amount of free, monomeric glucose should be at least 50% by weight, based on the solids content. An aqueous glucose solution containing at least 80% by weight of monomeric glucose, particularly preferably a content of more than 90% by weight of monomeric glucose, is preferred. In addition to the monomeric glucose, higher oligomeric and polymeric sugar components can also be present, depending on how they are formed in the hydrolysis of starch.

In addition to the aqueous glucose, other glycoses, for example fructose, mannose, galactose, talose, gulose, allose, altrose, idose, arabinose, xylose, lyxose and ribose can also be employed in their aqueous form at the given monomer contents. Glycose mixtures, oligosaccharides, for example maltose, lactose and multotriose, or mixtures of mono- and oligosaccharides can also be employed.

The water content in the aqueous glycoses is from 10 to 80% by weight, preferably from 15 to 60% by weight. Industrial solutions, in particular dextrose syrup, which have a water content of from 20 to 40% by weight are preferred.

The advantage in the use of aqueous glycoses lies not only in the easier availability of the glycose solutions, but also in the easier handling, particularly in the easier meterability into the preheated alcohol solution.

The aliphatic primary alcohols employed can have virtually any desired chain lengths, i.e. those from about 8 to about 30 carbon atoms. In order to obtain effective surface-active reaction products which can be employed as surfactant raw materials in detergents and cleaners, aliphatic primary alcohols having from 8 to 20 carbon atoms, in particular those having from 8 to 18 carbon atoms, are preferred. These higher aliphatic alcohols are preferably prepared from industrial fats. Of course, it is also possible, however, to employ synthetic primary alcohols such as oxo alcohols or Ziegler alcohols in the process of the invention.

The aliphatic primary ($C_8$- to $C_{18}$-alcohols, in particular $C_{12}$- to $C_{18}$-alcohols, particularly important as the alcohol component are preferably saturated and in particular straight-chain alcohols, such as can be obtained by the hydrogenation of native fatty acids on the industrial scale. An important aspect in the process of the invention is the preparation of surfactants which can be prepared exclusively from renewable raw materials. Typical representatives of the higher aliphatic alcohols which can be used in the process of the invention are, for example, n-octyl alcohol, n-nonyl alcohol, n-decyl alcohol, n-undecyl alcohol, n-dodecyl alcohol, n-tridecyl alcohol, n-tetradecyl alcohol, n-hexadecyl alcohol or n-octadecyl alcohol. Since the fatty alcohols preferably originate from natural fat sources, customarily mixtures of industrial fatty alcohols are also suitable as reactants.

In addition to the real fatty alcohols, branched-chain primary alcohols such as 2-ethylhexanol or such as oxo alcohols are also suitable for the reaction. Typical oxo alcohols are, for example, the compounds $C_{12}$-$C_{13}$-alkanol having about 25% of principally 2-methyl branching (Dobanol 23) and the corresponding $C_9$-$C_{11}$-alkanol (Dobanol 91).

The batch ratios are selected in such a manner that the molar ratio of aliphatic alcohol to glycose is from 2:1 to 10:1, preferably from 3:1 to 8:1, in particular from 3:1 to 6:1 (measure a).

The acidic catalyst having emulsifying properties employed is the acidic form of anionic surfactants (measure b). Particularly suitable representatives of such surfactants which may be mentioned are:

alkylbenzenesulfonic acids, in particular those of the formula

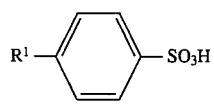

where $R^1=C_8$-$C_{22}$-alkyl (chain lengths of from $C_{12}$ to $C_{14}$ are particularly preferred);

alkylsulfonic acids, in particular those of the formula

where $R^2=C_8$-$C_{30}$-alkyl;

sulfosuccinic acid mono- or diesters, in particular those of the formula

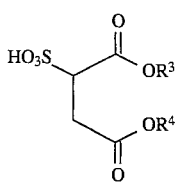

where $R^3$=H or $C_6$-$C_{22}$-alkyl and $R^4$=$C_6$-$C_{22}$-alkyl; sulfoalkylcarboxylic acids or -carboxylic acid esters, in particular those of the formula

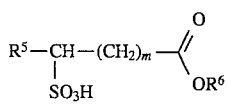

where $R^5$=$C_4$-$C_{22}$-alkyl, $R^6$=$C_1$-$C_{30}$-alkyl or H and m=0 to 10;

mono- and dialkylnaphthalenesulfonic acids, in particular those of the formula

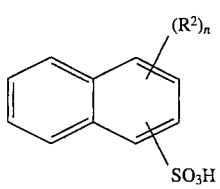

where $R^2$=$C_8$-$C_{30}$-alkyl and n=1 to 2.

If an acidic catalyst which can simultaneously act as an emulsifier for the glycose in the alcohol is not employed in the process of the invention, the process cannot be carried out. Thus, severe aggregation occurs, for example, with p-toluenesulfonic acid and polyglycoses are formed in increased amounts. Alkylbenzenesulfonic acids and here, in particular, benzenesulfonic acids having $C_{12}$- to $C_{14}$-alkyl radicals in the p-position are particularly preferred. The catalyst concentration is from 0.1 to 5% by weight, based on the amount of glycose employed. A catalyst concentration of from 0.5 to 2% by weight is preferred.

It has been found that on addition of a further emulsifier to the reaction solution in addition to the emulsifying acidic catalyst a distinct improvement of the process is achieved. The further emulsifiers employed for this purpose are alkyl glycosides, in particular alkyl glucoside (measure c).

Alkyl glycosides can be employed as solid substances or aqueous solutions. Advantageously, however, alcoholic solutions of alkyl glycosides are used. In a preferred embodiment, the process of the invention proposes that a fraction of the alkyl glycoside produced, which is present dissolved in the alcohol after conclusion of the glycosylation and neutralization, is retained and employed again in a following batch. As a result, the emulsifier does not have to be isolated. This procedure has the advantage that emulsification of the glycose is effected immediately at the start of the glycose addition due to the alkyl glycoside/alcohol mixture present in the reaction vessel. As a result, the glycose can be better reacted at the start of the addition phase and there is no turbidity or precipitation which can be attributed to increased formation of polyglycoses. If the emulsifier is omitted, considerable polyglycose formation occurs, i.e. the additional emulsifier is indispensable.

All alkyl glycosides which can be prepared by the process of the invention can be employed as the additional emulsifier. The emulsifiers are thus not restricted to glucose derivatives. The emulsifiers employed can be either pure alkyl monoglycosides, or technical mixtures of alkyl monoglycosides, alkyl oligoglycosides and polyglycoses. This does not impair their effectiveness.

Advantageously, as described above, an alcoholic solution of a technical alkyl glycoside mixture is used. As a basis of calculation for the amount of emulsifier employed in these alcoholic solutions, all sugar components (alkyl monoglycosides, alkyl oligoglycosides and polyglycoses) are summed and based on the glycose employed. Emulsifier concentrations of from 1 to 30% by weight, preferably from 1 to 15% by weight, can be employed. Concentrations of from 1.0 to 8% by weight are particularly preferred.

When carrying out the process of the invention, a procedure is used in which the aqueous glycose is preheated to 50°–90° C., better to 60°–70° C. (measure d). This leads to a distinct decrease in viscosity, so that the glycose can be added as an easily pourable liquid. In addition, a small temperature difference between added aqueous glycose solution and the reaction mixture is desirable in order to facilitate the supply of heat energy during the reaction.

The addition of the aqueous glycose solution is carried out in portions or, better, continuously. The continuous addition is advantageously controlled in such a manner that the water introduced and the water resulting from the reaction is simultaneously removed by distillation under reduced pressure. In this process, the reaction is carried out in the heterogeneous phase with the formation of a stable glucose syrup/alcohol emulsion, particular caution during the addition for continuous formation of a homogeneous phase, as described in U.S. Pat. No. 4,996,306, not having to be maintained. Only good emulsification of the added glycose syrup has to be ensured. This can be achieved in a simple manner using the emulsifying additives already described (emulsifying acid, alkyl glycoside as emulsifier). A further effective measure for good emulsification is achieved by effective stirring of the reaction mixture, which is preferably effected on the laboratory scale by means of baffles and disk mixers.

In pilot plant and full-scale batches, recycling apparatus through an external liquid circulation has proven particularly suitable and in addition has the advantage that the heat energy can be carefully added by means of a heat exchanger and high vessel wall temperatures can thus be avoided. Adverse effects of temperature control on the colour of the product can thus be prevented.

Feeding-in or addition of the glucose syrup to the recycling line via a liquid jet pump has proven particularly advantageous. By appropriate choice of the recycling efficiencies (drive jet) and the dosage rate, optimum emulsification can be achieved so that virtually no precipitation of polyglycose in the reactor can be detected.

Surprisingly, it has been possible to determine that, during the described heterogeneous direct procedure with the formation of an emulsion, the product quality with respect to, for example, monoglucoside content, polyglycose and color is better than with transacetalization methods known from the literature (cf. Example D). Even small particle-like precipitations of polymeric products (mainly polyglycose) do not impair the product quality. However, the particle-like precipitations must be below 2% by weight with respect to isolated product, since otherwise scorching and color damage of the product occur during distillation on the one hand, and on the other hand the yields of alkyl monoglucoside are lower (see Comparative Examples A, B and C).

In principle, particle-like precipitations of polyglycose of this type can of course be removed by filtration of the crude product (cf. Comparative Example A), which means, however, an additional process step. In the above process, however, this is not necessary in the case of small precipitations (<2% by weight with respect to isolated product).

Since in the present process the product quality is neither impaired by working in heterogeneous phase with the formation of a stable emulsion nor by the formation of small precipitations, the process represents a simplified, economical route for the synthesis of alkyl polyglycosides and thus an improvement of the prior art.

The reaction mixture of alcohol, acidic catalyst and alkyl glycosides is preheated to 100°–150° C., better 110°–120° C., before the start of glycose addition and the reaction is carried out in this temperature range (measure e). The water addded with the glycose addition and the water formed during the acetal formation is continuously removed from the emulsion by distillation under reduced pressure (measure e). Depending on the higher alcohol employed, the pressure is selected to be from 10 to 100 mbar. The higher the boiling point of the alcohol or alcohol mixture employed, the lower can be the reduced pressure selected. For instance, with a straight-chain $C_8/C_{10}$ alcohol mixture a reduced pressure of expediently from 50 to 60 mbar is selected, while with a $C_{12}/C_{14}$ alcohol mixture a reduced pressure of from 30 to 40 mbar is preferred.

After conclusion of the glycose addition, the mixture is expediently stirred for a further 10 min–2 h in the temperature range indicated. The content of free glycose in the reaction solution has then normally fallen to below 0.5% by weight, i.e. the glycose has virtually completely reacted.

Suitable neutralizers for deactivating the acidic catalyst after the reaction (measure f) are in particular basic alkali metal, alkaline earth metal or aluminum salts, the anions of which can be of organic or inorganic nature. Examples of bases of this type are sodium hydroxide, potassium hydroxide, calcium hydroxide, aluminum hydroxide, sodium acetate, sodium methoxide and sodium ethoxide. The use of aqueous sodium hydroxide solution is preferred, since this can be easily incorporated into the alcohol/product mixture, can be easily added and does not require a filtration step for salts which may precipitate. The neutralization is carried out so that a slightly basic solution of pH 8–10, measured as a 1:1 mixture of water:fatty alcohol/product, is then present. For neutralization, the hot reaction solution is expediently cooled somewhat beforehand, for example to 70°–100° C.

The distillation of the excess alcohol (measure g) is carried out by known techniques which are gentle to the process product, for example by means of a thin layer evaporator, and at from 0.01 to 10 mbar, the pressure being dependent on the boiling point of the alcohol or alcohol mixture employed. For this purpose, a prior filtration of, for example, precipitated polyglycose is not as a rule necessary.

The almost alcohol-free product obtained is processed by addition of water to give a 30–70% strength by weight, preferably about 50% strength by weight, aqueous paste and bleached with a compound which eliminates active oxygen such as, for example, 30% strength by weight aqueous hydrogen peroxide solution (measure h). The bleaching is customarily carried out at from 70° to 90° C., the pH during the bleaching process being checked and optionally adjusted to values of from pH 8 to pH 10 using, for example:, sodium hydroxide. The amount of hydrogen peroxide used is as a rule 0.3–3% by weight, calculated as $H_2O_2$ and based on the amount of the product after removal of the alcohol.

The present invention is a combination of the individual measures (a) to (h), the individual measures partly already being known as such from the prior art. The carrying-out of the glycosylation in two phases, which are present as anemulsion and contain virtually no polyglycose or less than 2% by weight of polyglycose, is new. The advantage of the process of the invention lies in the combination of several individual advantages originating from the individual measures (a) to (h), whose interaction leads to an outstanding and surprising overall result.

Using the process of the invention, an outstanding product quality is in particular obtained, and the alkyl glycosides prepared are only faintly colored and contain only a small amount of alkyl oligo- and polyglycosides.

Easily available and readily handleable aqueous glycoside solutions can advantageously be used as starting materials and resort no longer has to be made to solid glycosides which are dehydrated by troublesome processes and optionally processed to specific particle sizes.

The process of the invention is easy and problem-free to carry out, there are, for example, no addition problems or difficulties during the supply or removal of heat, also troublesome filtration processes are normally not necessary. The process is simple, and it is achieved with a minimum of chemical reactants and a minimum of process measures. The process works at high efficiency with respect to the space-time yield, and the products obtained are sufficiently pure. The process is thus to a great extent economical.

The process of the invention finally permits problem-free transfer to the large industrial scale without scaling-up problems.

EXAMPLES

Parts and percentages are by weight.

Example 1

825 g of dodecanol (4.57 mol) were initially introduced into a 2-1 multi-necked stirrer reactor with a baffle,-disk mixer, thermometer, distillation head and a metering unit, consisting of a metering pump, pressure-retaining valve and a nozzle, and 2.6 g (0.008 mol) of dodecylbenzenesulfonic acid were added thereto. This mixture was treated with 121.6 g of an alkyl glucoside/dodecanol emulsifier mixture (composition: 63% dodecanol (0.41 mol), 22.6% $C_{12}$-monoglucoside, 5.2% $C_{12}$-diglucoside, 2.2% $C_{12}$-triglucoside, 0.7% $C_{12}$-tetraglucoside, <0.5% $C_{12}$-pentaglucoside and 5.9% polyglucose). In this case, the glucose-containing proportions of the emulsifier were 30% with respect to the gluocose employed. The molar ratio of fatty alcohol to glucose was 6:1.

The solution was heated to 115°–120° C. 214 g (0.83 mol) of a dextrose syrup heated to 60° C. (70% strength solution, glucose content about 99.5%) were continuously metered in under reduced pressure at from 30 to 35 mbar so that a cloudy emulsion was formed which contains virtually no particle-like precipitations of polyglucose. At the same time, both the water added with the syrup and the water produced in the reaction was removed to equilibrium by distillation at the given reduced pressure. It was important in this connection that an optimum distribution of the dextrose syrup in the fatty alcohol was ensured by the combination of disk mixer (200 rpm), baffle and metering by means of a nozzle. After a metering time of 4 h and a stirring time of 30 min, 83 g of water were removed by distillation. A slightly turbid, pale-yellow reaction solution was obtained.

After cooling to 90° C., the catalyst was deactivated using 1.6 g of 50% strength sodium hydroxide solution; the resulting solution had a pH of 8.3 (measured in 50% strength aqueous solution). The excess alcohol was removed by means of a thin layer evaporator (heating temperature 170° C., outlet temperature 140° C.) under a reduced pressure of 1 mbar. The amount of distillate was 820 g. The product (240 g) was processed directly in paste form by addition of water to give a 50% strength aqueous solution and bleached at 80° C. using 12.3 g of $H_2O_2$ (30% strength solution). The iodine color number was 15. The composition of the product is shown in the Table given below.

Comparative Example A (p-toluenesulfonic acid as catalyst)

The dodecylbenzenesulfonic acid in Example 1 was replaced by 1.5 g (0.008 mol) of p-toluenesulfonic acid. After the metering of the dextrose syrup, a highly turbid crude product permeated with solid particles was obtained with a procedure similar to Example 1. Filtration gave 25 g of residue which consisted to about 80% of polyglucose. The filtrate (210 g) worked up in a manner similar to Example 1 had the composition shown in the Table given below.

Comparative Example B (poor dispersion)

Example 1 was repeated, only in contrast to Example 1 a dropping funnel was employed instead of the nozzle to meter the dextrose syrup. After metering of the syrup, a turbid solution was obtained which contained considerable agglutinations. Filtration gave 64 g of residue (about 80% polyglucose).

Dispensing with the baffle and disk mixer led to a still poorer dispersion of the dextrose syrup. Over 50% of the glucose was isolated as polyglucose after filtration.

Examples 2 to 5

The procedure was as in Example 1 with variation of the alkyl glucoside concentration. The results are summarized in the Table given below.

Comparative Example C (without alkyl glucoside as emulsifier)

Example 1 was repeated., only in contrast to Example 1 no alkyl glucoside was added as additional emulsifier. After metering of the dextrose syrup, a turbid solution permeated with solid particles was present. 47 g of residue which consisted to over 80% of polyglucose were removed by filtration. The filtrate (195 g) worked up in a manner similar to Example 1 had the composition shown in the Table given below.

Example 6

Corresponding to Example 4, 606 g of dodecanol (3.25 mol), 16.7 g of the same alkyl glucoside/dodecanol emulsifier mixture as in Example 1 (3% based on glucose employed) and 2.6 g (0.008 mol) of dodecylbenzenesulfonic acid were reacted with 214 g (0.83 mol) of the same dextrose syrup as in Example 1 with the formation of an emulsion. The molar ratio of fatty alcohol to glucose was 4:1. After removal of water, a slightly turbid solution was obtained. Distillation gave 500 g of distillate and 245 g of product which after bleaching with 30% strength $H_2O_2$ solution (12.3 g) had an iodine color number of 13 (as a 50% aqueous paste). The composition of the product is shown in the Table given below.

Examples 7 and 8

The procedure was as in Example 6 with further variation of the molar ratio of fatty alcohol to glucose. The results are summarized in the Table given below. They show that the alkyl monoglucoside content falls and the polyglucose content rises with decreasing molar ratios. An acceptable ratio between product composition and making full use of the flask or vessel volume is achieved at molar ratios of 3:1 to 4:1.

TABLE

Conditions and results of Experiments 1 to 8 and Comparative Examples A to C

| Ex. | Alkyl glucoside conc. (% based on glucose) | $C_{12}OH$:glucose | Yield | $C_{12}OH$ % | $C_{12}$—Glu % | $C_{12}$—Fru % | $C_{12}$—Glu$_2$ % | $C_{12}$—Glu$_3$ % | $C_{12}$—Glu$_4$ % | Poly-glucose % | Iodine color number of the product (50% strength aqueous solution) |
|---|---|---|---|---|---|---|---|---|---|---|---|
| 1 | 30 | 6:1 | 240 g | 1.5 | 52.0 | 2.0 | 14.0 | 6.0 | 2.0 | about 20 | 15 |
| A* | 30 | 6:1 | 210 g | 1.8 | 42.0 | 1.5 | 10.5 | 6.5 | 2.5 | about 25 | 34 |
| B** | 30 | 6:1 | — | — | — | — | — | — | — | mainly | — |
| 2 | 15 | 6:1 | 235 g | 2.0 | 54.0 | 1.5 | 14.5 | 6.3 | 2.0 | about 18 | 21 |
| 3 | 7.5 | 6:1 | 242 g | 2.0 | 58.5 | 2.1 | 13.2 | 5.9 | 1.8 | about 15 | 14 |
| 4 | 3 | 6:1 | 252 g | 1.4 | 64.5 | 2.2 | 12.9 | 5.9 | 2.0 | about 10 | 11 |
| 5 | 1.5 | 6:1 | 237 g | 1.8 | 60.8 | 1.8 | 13.2 | 5.8 | 1.5 | about 14 | 21 |
| C*** | 0 | 6:1 | 195 g | 1.7 | 56.7 | 1.7 | 12.8 | 4.2 | 1.3 | about 21 | 45 |
| 6 | 3 | 4:1 | 245 g | 1.7 | 55.5 | 1.2 | 14.8 | 7.1 | 2.4 | about 15 | 13 |
| 7 | 3 | 3:1 | 225 g | 2.0 | 48.1 | 1.0 | 16.0 | 7.4 | 3.0 | about 21 | 17 |
| 8 | 3 | 2:1 | 205 g | 1.1 | 41.3 | 0.8 | 19.2 | 6.9 | 2.5 | about 28 | 22 |
| D**** | 0 | | 238 g | 1.5 | 53.0 | 1.8 | 11.0 | 5.1 | 1.5 | about 20 | 20 |

Explanatory notes to the Table:
*additional residue of 25 g (about 80% polyglucose)
**polyglucose as predominant product
***additional residue of 47 g (>80% polyglucose)

TABLE-continued

Conditions and results of Experiments 1 to 8 and Comparative Examples A to C

| Ex. | Alkyl glucoside conc. (% based on glucose) | $C_{12}OH$: glucose | Yield | Composition of the product | | | | | | | Iodine color number of the product (50% strength aqueous solution) |
|---|---|---|---|---|---|---|---|---|---|---|---|
| | | | | $C_{12}OH$ % | $C_{12}$—Glu % | $C_{12}$—Fru % | $C_{12}$—$Glu_2$ % | $C_{12}$—$Glu_3$ % | $C_{12}$—$Glu_4$ % | Poly-glucose % | |

****6.0% butyl glucoside containing
$C_{12}OH$ = dodecanol, $C_{12}$—$Glu_2$ = dodecyl monoglucoside,
$C_{12}$Fru = dodecyl monofructoside, $C_{12}Glu_2$ = dodecyl diglucoside, $C_{12}Glu_3$ = dodecyl triglucoside,
$C_{12}Glu_4$ = dodecyl tetraglucoside

Example 9

Corresponding to Example 6, 630 g of Lorol 1214 special (fatty alcohol mixture, from Henkel containing about 75% dodecanol, about 23% tetradecanol and about 1% hexadecanol; OH number=295 mg of KOH/g) were employed as the alcohol component. The emulsifier concentration was 3%, based on glucose employed. The composition of the emulsifier was 64% $C_{12}/C_{14}$ alcohol, 23% alkyl monoglucoside, about 5% alkyl diglucoside, about 2% alkyl triglucoside, <0.5% alkyl tetra- and alkyl pentaglucoside, and about 5% polyglucoside (alkyl: $C_{12}/C_{14}/C_{16}$ mixture). After addition of dextrose syrup, the reaction mixture is present as an emulsion. Removal of water from this gives a slightly turbid solution. After distillative working-up and bleaching with 30% strength $H_2O_2$ solution (14.7 g), 510 g of product were obtained as a 50% strength aqueous solution having an iodine color number of 9. The composition of the product was 1.9% $C_{12}/C_{14}$ alcohol; 57% dodecyl/tetradecyl monoglucoside, 1.9% dodecyl/tetradecyl fructoside, 14.4% dodecyl/tetradecyl diglucoside, 7.7% dodecyl/tetradecyl triglucoside, <3% dodecyl/tetradecyl tetra- and pentaglucoside, about 15% polyglucose and <0.5% free glucose. The hexadecyl contents were not analyzed.

Other native alcohol mixtures such as $C_8/C_{10}$ or $C_{10}/C_{12}$ alcohol mixtures (for example Lorol C 8–10 or Lorol C 10–12 from Henkel) gave an analogous spectrum in the product composition.

Comparative Example D

In a manner similar to the prior art disclosed in EP-A-0,301,298, an alkyl polyglucoside based on dodecanol was prepared by the transacetalization method via the butyl glucoside intermediate. The molar ratios butanol: glucose::dodecanol were 6:1:6. The composition of the product can be taken from the Table and shows clearly that a qualitatively better product can be prepared using the described direct procedure.

Example 10

A 335 l enamel vessel with an impeller stirrer and an external recycling apparatus consisting of a recycling-line and conveyor pump was used. A liquid jet pump (Wiegand) for metering the glucose syrup was incorporated into the recycling line.

The following amounts of substance were employed:
150 kg of Lorol 1214 special (cf. Example 9)
4.2 kg of emulsifier mixture (composition similar to Example 9)
0.6 kg of dodecylbenzenesulfonic acid
51.5 kg of glucose syrup (70% strength aqueous solution)

Lorol 1214 special, emulsifier mixture and catalyst were initially introduced into the reactor, heated to 115° to 120° C. and mixed at a recycling capacity of 600 l/h. Glucose syrup preheated to 60° C. was metered in over the course of 4 h by means of the liquid jet pump and solvent water and water of reaction were simultaneously removed by distillation at from 40 to 50 mbar. The amount of water removed was 20.2 kg. The mixture was stirred for 30 min after metering of the syrup had ended, almost no particle precipitations of polyglucose being found (<1% based on final product). The mixture was subsequently neutralized with 200 g of 50% strength aqueous sodium hydroxide solution. After distillative working-up and bleaching of the product using 30% strength $H_2O_2$ solution (0.8 kg), 115 kg of product were obtained as a 50% strength aqueous solution (iodine color number 7). The composition of the product was 1.6% residual alcohol, 56.5% dodecyl/tetradecyl monoglucoside, 2.1% dodecyl/tetradecyl fructoside, 13.3% dodecyl/tetradecyl diglucoside, 7.5% dodecyl/tetradecyl triglucoside, <3% dodecyl/tetradecyl tetra- and pentaglucoside, about 16% polyglucose and <0.5% free glucose. The hexadecyl contents were not analyzed.

We claim:

1. An emulsion process for preparing alkyl glycosides by reaction of aqueous glycoses having a water content of 10–80% by weight with aliphatic primary alcohols having from 8 to 30 C atoms, which comprises
   (a) employing the alcohols and the glycoses in a molar ratio of 2:1–10:1,
   (b) using 0.1–5% by weight, based on the amount of the glycoses employed, of an acidic catalyst selected from the group consisting of

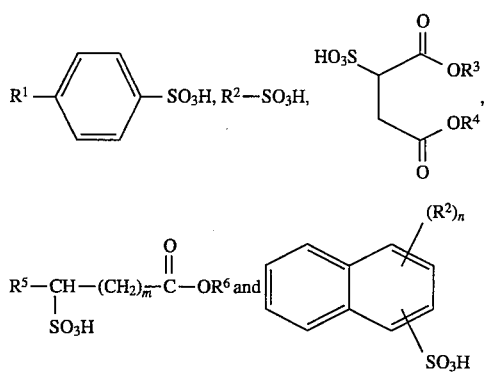

wherein $R^2$ is $C_8$-$C_{22}$ alkyl, $R^2$ is $C_8$-$C_{30}$ alkyl, $R^3$ is H or $C_8$-$C_{22}$-alkyl, $R^4$ is $C_6$-$C_{22}$, alkyl, $R^5$ is $C_4$-$C_{22}$- alkyl, $R^6$ is $C_1$-$C_{30}$ alkyl or H, m is an integer from 0 to 10 and n is 1 or 2, (c) using 1–30% by weight, based on the amount of the glycoses employed, of alkyl glycosides as an emulsifier, (d) preparing the aqueous glycose to 50°–90° C. and metering the preheated aqueous solution of the glycose with effective mixing into the reaction mixture of alcohol, acidic catalyst and emulsifier in such a manner that an emulsion is formed, (e) carrying out the reaction in emulsion at from 100° to 150° C. and from 10 to 100 mbar, the water introduced into the reaction mixture and the water formed by the reaction being continuously removed by distillation, (f) after the reaction has ended, neutralizing the acidic catalyst by addition of a base such that the resulting mixture has a pH of 8–10, then (g) removing the excess alcohol by distillation at from 0.01 to 10 mbar down to a residual content of less than 5% by weight, based on the amount of alkyl glycoside present, and (h) bleaching the reaction mixture at pH 8–10 after conversion into an aqueous paste having a content of 30–70% by weight of alkyl glycoside using a compound eliminating active oxygen.

2. A process for preparing alkyl glycosides as claimed in claim 1, wherein the aqueous glycose contains glucose.

3. A process for preparing alkyl glycosides as claimed in claim 1 or 2, wherein the alcohols employed are aliphatic primary alcohols having from 8 to 20 C atoms.

\* \* \* \* \*